United States Patent [19]

de Figueiredo

[11] 4,294,248

[45] Oct. 13, 1981

[54] DEVICE FOR AUTOMATICALLY CONTROLLING THE INFUSION LIQUID FLOW IN AN INFUSION APPARATUS

[76] Inventor: Nuno R. M. de Figueiredo, Högstigen 5, 182 74 Stocksund, Sweden

[21] Appl. No.: 85,281

[22] Filed: Oct. 16, 1979

[30] Foreign Application Priority Data

Oct. 19, 1978 [SE] Sweden .............................. 7810917

[51] Int. Cl.³ ............................................. A61M 5/6
[52] U.S. Cl. ................................................ 128/214 E
[58] Field of Search ...................... 128/214 E, DIG. B

[56] References Cited

U.S. PATENT DOCUMENTS 4,094,318 6/1978 Burke et al. ..................... 128/214 E
4,137,913 2/1979 Georgi ............................ 128/214 E

FOREIGN PATENT DOCUMENTS 2419520 12/1974 Fed. Rep. of Germany ... 128/214 E

Primary Examiner—William E. Kamm
Attorney, Agent, or Firm—Fleit & Jacobson

[57] ABSTRACT

In an infusion apparatus, the infusion liquid flow is automatically controlled by means of a control equipment which successively adjusts the actual value of said flow towards a desired value of said flow. In order to facilitate an infusion of a preselected total infusion liquid volume within a predetermined total time, the desired value of the infusion liquid flow, in its turn, is successively adjusted in response to a successively calculated value of the instantaneously remaining portion of the selected total infusion liquid volume.

7 Claims, 1 Drawing Figure

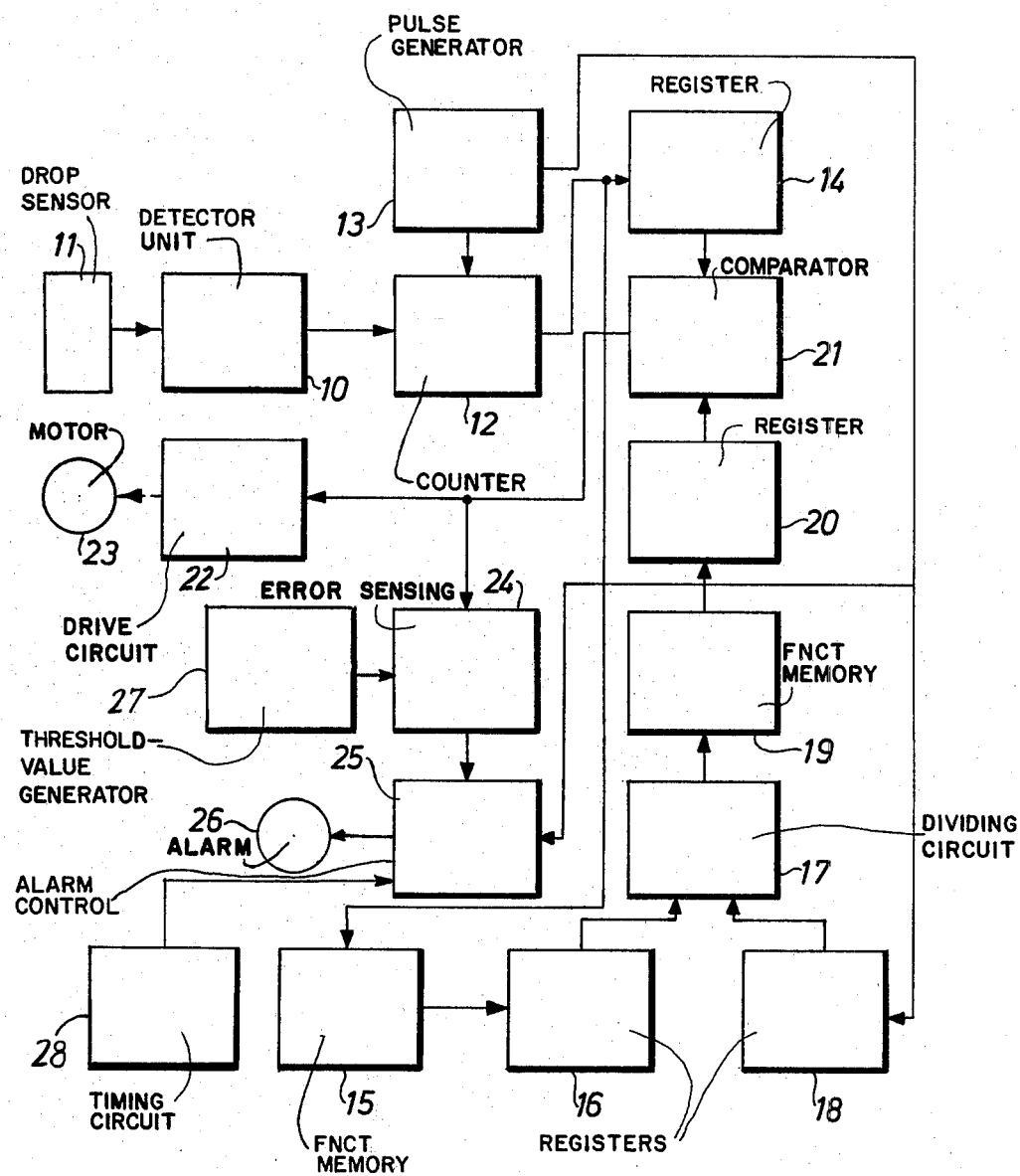

DEVICE FOR AUTOMATICALLY CONTROLLING THE INFUSION LIQUID FLOW IN AN INFUSION APPARATUS

The present invention relates to a device for automatically controlling the infusion liquid flow in an infusion apparatus by successively adjusting the actual value of said flow towards a desired value of said flow.

A common feature of prior art devices of the kind above specified, such as those disclosed in British Pat. Nos. 1,109,175 and 1,253,817 and U.S. Pat. No. 3,450,153, is that they utilize a fixed desired value of the infusion liquid flow during the entire infusion process. This means that the total time for the infusion of a certain selected total liquid volume may vary considerably due to variations in the liquid flow, occurring in spite of the automatic control of said flow, and as a consequence of temporary breaks in the infusion, for instance in connection with another treatment or an examination of the patient. In practice, such variations in the total infusion time may be very unfavourable as it may often be of great importance that a patient is given the intended liquid volume within a certain predetermined time.

The invention has for its object to provide an improved device of the kind initially specified, which eliminates the above drawback. In accordance with the invention, for this purpose, the device may be arranged to adjust the desired value of the infusion liquid flow successively in response to a successively calculated value of the instantaneously remaining portion of a preselected total liquid volume intended for infusion during a given total time. By adjusting the desired value of the infusion liquid flow successively in response to the instantaneously remaining portion of the total infusion liquid volume, it is possible to provide such an automatic control of the infusion liquid flow that the desired liquid volume will actually be infused within the intended time.

The device may suitably be arranged to calculate said value of the instantaneously remaining portion of the selected total infusion liquid volume through subtraction of a total value or successive partial values of the infused liquid quantity from the value of the total infusion liquid volume.

The invention may advantageously be applied on a device for automatically controlling the infusion liquid flow in an infusion apparatus wherein said flow is formed by a series of successive drops, the device being then arranged to control the infusion liquid flow by successively adjusting the actual value of the drop rate towards a desired value thereof. In this case, the device may be arranged to calculate said total value or said partial values, respectively, of the infused liquid quantity as well as a desired value of the drop rate, corresponding to the value of the instantaneously remaining portion of the selected total infusion liquid volume, with the aid of stored information about the interrelationship between the drop rate and the volume of each individual drop, which varies in response to the drop rate.

It should be noted that, in the present specification as well as in the claims, the term drop rate is intended to cover various possible expressions for the time dependency of the drop formation. Thus, the drop rate may be expressed in drop frequency as well as in drop period, i.e. the time interval between mutually corresponding phases or stages during the formation of two successive drops.

In a manner, known per se, the device may further be arranged to provide an alarm indication upon an inadmissibly large deviation in the actual value of the infusion liquid flow from the desired value of said flow. In this case, the device may suitably be arranged to cause an alarm indication only when the duration of such an inadmissible deviation exceeds a permitted length of time for the occurrance of such a deviation. The permitted length of time may be selectable. Additionally, the limits for admitted deviations in the actual value of the infusion liquid flow from the desired value may also be selectable.

Below the invention will be described in further detail, reference being had to accompanying drawing, showing a block diagram of a device according to an embodiment of the invention, selected by way of example.

In the drawing, reference numeral 10 designates a pulse generating detector unit, the input of which is intended to be connected to a primary drop detector 11, such as an electro-optical sensor, and serving to sense the drop rate in the drop chamber of an infusion apparatus, wherein a controllable infusion liquid flow is formed by a series of drops successively generated in the drop chamber. The general design and function of such an infusion apparatus is well-known in the art, for instance through British Pat. Nos. 1,109,175 and 1,253,817 and U.S. Pat. No. 3,450,153, and hence, it need not be described herein. Detector unit 10 is arranged to deliver a short pulse over its output each time it receives a signal from drop sensor 11, indicating the passage of a drop through the drop chamber.

The output signal from detector unit 10 is fed to a control input of a counter 12, the principal input of which is connected to a clock pulse generator 13. Counter 12 consists of an UP-counter which counts the supplied clock pulses in an ascending order. When counter 12 receives a pulse from detector unit 10 on its control input, it will deliver an output signal representing a number corresponding to its instantaneous counting state to a register 14, in which said number will be stored. Counter 12 is then automatically reset in order to start counting the supplied clock pulses in an ascending order again. Register 14 may consist of a latch memory.

The number fed to and stored in register 14, which number will be maintained in said register until a new number is supplied from counter 12, represents the actual value $T_{act}$ of the time interval between two successive drops formed in the drop chamber of the infusion apparatus.

The output signal from counter 12 is also fed as a control and addressing signal to a function memory 15 in which values of the volume of each individual drop corresponding to different values of the drop rate (or the time interval between successive drops) are stored in different portions of the memory. The signal delivered from counter 12 to memory 15, which consists of a read-only memory, gives rise to an output signal from said memory. Said output signal represents a stored value $\Delta V$ of the drop volume corresponding to the occurring drop rate, said value $\Delta V$ being obtained from the portion of memory 15 addressed by the signal from counter 12.

Reference numeral 16 designates a register of accumulating type, in which information about the total liquid volume to be infused during an infusion process is stored before starting said process. Said register 16 is arranged to be supplied with successive output signals from memory 15. Each time an input signal is received from memory 15, the number stored in register 16 will be reduced by the value ΔV of the volume of a drop passing through the drop chamber of the infusion apparatus represented by said input signal. Hereby the information stored in register 16 will continuously represent the value of the instantaneously remaining portion of the total infusion liquid volume. The output of register 16 is connected to a first input of a dividing circuit 17.

Reference numeral 18 designates a register formed by a DOWN-counter. Before the initiation of an infusion process, information is stored in register 18 about a predetermined total time, during which the total infusion liquid volume should be infused. Register 18 has an input connected to clock pulse generator 13 to receive clock pulses therefrom. The received clock pulses will cause register 18 to count in a descending order, whereby the value stored in said register will be brought to represent the instantaneously remaining portion of the predetermined total infusion time. The output of register 18 is connected to a second input of dividing circuit 17.

The dividing circuit 17 is arranged to generate an output signal representing the ratio between the remaining portion of the selected total infusion liquid volume and the remaining portion of the predetermined total infusion time. Said signal is supplied as a control and addressing signal to a function memory 19, in which desired values $T_{des}$ of the time interval between two successive drops, corresponding to different values of said ratio, are stored in different portions of the memory. Memory 19, which consists of a read-only memory, has an output connected to a further register 20. Over said output, memory 19 will deliver an output signal representing the desired value $T_{des}$ of the time interval between two successive drops corresponding to the desired drop rate, said value being obtained from the portion of memory 19 addressed by the signal received from circuit 17. Thus, register 20 will contain information about the desired value $T_{des}$ of the time interval between two successive drops while register 14 will contain information about the actual value $T_{act}$ of said time interval.

The outputs of register 14 and 20 are connected each to one input of a comparator 21, which is arranged to compare said two $T_{des}$ and $T_{act}$ values with each other and to deliver a control signal corresponding to the difference between said two values to a drive circuit 22, serving to supply drive signals to a motor 23. Said motor 23 is arranged to control the drop rate in the drop chamber of the infusion apparatus in any suitable manner. For instance, motor 23 may actuate clamping means adapted to provide a variable clamping action on a flexible tube forming a passage for the infusion liquid. Such clamping means are previously known, for instance through the three patent specifications above referred to.

The device above described facilitates such a control of the drop rate and, hence, of the infusion liquid flow that it will be possible to make sure that the selected total infusion liquid volume will actually be infused during the desired total infusion time.

Reference numeral 24 designates an error sensing circuit which is connected to the output of comparator 21 and adapted to sense the deviation between the actual value of the drop rate and the desired value of said rate. The error sensing circuit 24 may suitably contain a threshold-value generator 27, adapted to generate a threshold value which the input signal to circuit 24 must exceed in order to give rise to an output signal from said circuit. Hereby the limits for an admissible deviation of the actual value of the drop rate from the desired value of said rate may be selected so as to cause circuit 24 to deliver an output signal only when the actual value of the drop rate deviates to an inadmissible extent from the desired value of the drop rate. The output signal from circuit 24 is supplied to an alarm control unit 25 which serves to actuate an alarm means 26. Said alarm means 26 may preferably be arranged to provide a visual or acoustic alarm. Alarm control unit 25 may contain an adjustable timing circuit 28 operating in such a manner as to cause an actuation of alarm means 26 only when an error signal received from circuit 24 has a duration exceeding a certain, preferably selectable length of time.

The invention is not restricted to the embodiment above described and shown in the drawing. Instead, many modifications are feasible within the scope of the invention. For instance, memories 15 and 19 may be replaced by suitable arithmetic logical units.

I claim:

1. A device for automatically controlling infusion liquid flow in an infusion apparatus comprising first means for successively adjusting the actual value of said flow towards a desired value of said flow, second means for successively adjusting said desired value of the flow, and third means for successively calculating the value of the instantaneously remaining portion of a preselected total infusion liquid volume intended for infusion during a given total time, said second means being responsive to said third means.

2. A device according to claim 1, wherein said third means comprises means for calculating successive partial values of infused liquid quantity, and means for subtracting the successive partial values of the infused liquid quantity from the value of the total infusion liquid volume.

3. A device according to claim 2, for use in conjunction with an infusion apparatus wherein the infusion liquid flow is formed by a series of successive drops, said first means being arranged to control the infusion liquid flow by successively adjusting the actual value of the drop rate towards a desired value of said rate, means for storing information about the interrelationship between the drop rate and the volume of each individual drop, said second and third means being arranged to calculate said partial values of the infused liquid quantity as well as a desired value of the drop rate corresponding to the value of the remaining portion of the selected total infusion liquid volume with the aid of the stored information.

4. A device according to any of the preceding claims, comprising means for sensing an inadmissible deviation in the actual value of the infusion liquid flow from the desired value of said flow, alarm means for causing an alarm indication upon sensing of the inadmissible deviation, and means for determining a permitted length of time for an inadmissible deviation, said alarm means causing an alarm indication only when the duration of such an inadmissible deviation exceeds the permitted length of time for the occurrence of such a deviation.

5. A device according to claim 4, characterized in that said permitted length of time is selectable.

6. A device usable with an infusion apparatus for automatically controlling infusion of a predetermined volume of liquid in a predetermined time period comprising:
- means for sensing and for generating a volume change signal representative of the rate of liquid flow;
- means for storing a value representative of the predetermined volume and for generating a volume remaining signal representative of the stored value, said storing and generating means being responsive to said volume change signal so that the stored value represents the remaining volume to be infused;
- means for storing a value representative of the predetermined time period, for reducing the stored value to represent the remaining time period, and for generating a time remaining signal representative of the stored value;
- ratio means for dividing the volume remaining signal by the time remaining signal to obtain a ratio signal representative of a desired liquid flow rate;
- means for comparing the ratio signal and the volume change signal and for generating a control signal representative of the comparison; and
- means responsive to said control signal for adjusting the infusion apparatus to thereby control the rate of liquid infusion.

7. A device for automatically controlling infusion liquid flowing in a series of successive drops comprising:
- means for sensing individual drops and for generating an elapsed time signal representative of the time interval between successive drops;
- first register means (18) for storing and for generating a time remaining signal representative of the amount of total liquid infusion time, the amount being reduced during liquid flow to indicate the remaining portion of total infusion time;
- first function means (15) responsive to said elapsed time signal for generating a volume dispensed signal representative of the volume of individual sensed drops, said first function means including means for storing values of volumes of individual drops corresponding to different time intervals between successive drops;
- second register means (16) for storing the value of the remaining volume of liquid to be infused, said register means being responsive to said volume dispensed signal from said first function means to generate a volume remaining signal;
- dividing means (17) for dividing said volume remaining signal by said time remaining signal to obtain a ratio signal;
- second function means (19) responsive to said ratio signal from said dividing means for generating a desired time interval signal representative of the desired time interval between successive drops, said second function means including means for storing values of time intervals between successive drops corresponding to different ratios;
- comparator means (21) for comparing said desired time interval signal and said elapsed time signal and for generating a control signal representative of the comparison; and
- means responsive to said control signal for controlling the time interval between successive drops.

* * * * *